(12) United States Patent
Kretschmer Schmid

(10) Patent No.: US 7,569,229 B2
(45) Date of Patent: *Aug. 4, 2009

(54) MONOCYTE LOCOMOTION INHIBITORY FACTOR

(75) Inventor: Roberto Rodolfo Kretschmer Schmid, Pedregal (MX)

(73) Assignee: Center for Blood Research, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/040,253

(22) Filed: Feb. 29, 2008

(65) Prior Publication Data

US 2008/0167253 A1    Jul. 10, 2008

Related U.S. Application Data

(63) Continuation of application No. 10/861,123, filed on Jun. 4, 2004, now Pat. No. 7,514,090, which is a continuation-in-part of application No. 10/263,947, filed on Oct. 3, 2002, now Pat. No. 7,078,044, which is a continuation of application No. 09/342,956, filed on Jun. 29, 1999, now Pat. No. 6,254,591.

(30) Foreign Application Priority Data

Jun. 29, 1998    (MX) ...................... 985265

(51) Int. Cl.
*A61K 39/05* (2006.01)
*C07K 5/00* (2006.01)

(52) U.S. Cl. ...................... 424/269.1; 424/9.1; 424/9.2; 424/265.1; 530/300

(58) Field of Classification Search ........................ None
See application file for complete search history.

(56) References Cited

U.S. PATENT DOCUMENTS 6,524,591 B1 *   2/2003   Schmid ................... 424/265.1

7,078,044 B2    7/2006   Schmid

OTHER PUBLICATIONS

Moralez-Martinez et al. Molecular and Biochemical Parasitology, 2008, vol. 158, p. 46-51.*
Delgado et al. (Nature 2001, vol. 7, p. 563-568.*
Savoldo et al, Blood, vol. 108, p. 2942-2949.*
Baker et al. Gene Therapy, 2003, vol. 10, p. 844-853.*
Rico, et al., "Production of the Monocyte Locomotion Inhibitory Factor (MLIF) By Axenically Grown Entamoeba Histolytica: Synthesis or Degradation?" Archives of Medical Research 28:S235-S236 (1997).
Kretschmer, et al., "Inhibition of Human Monocyte Locomotion By Products of Axenically Grown E. Histolytica," Parasite Immunology, 1985, pp. 527-543.
Rico, et al., The Monocyte Locomotion Inhibitory Factor (MLIF) Produced by Axenically Grown Entamoeba Histolytica Fails to Affect the Locomotion and the Respiratory Burst of Human Eosinophils In Vitro, Archives of Medical Research, vol. 28, Suppl., pp. S233-S234, 1997.
Kretschmer, et al., "The Role of Mannose In the Receptor of the Monocyte Locomotion Inhibitory Factor Produced by Axenically Grown Entamoeba Histolytica," Parasitology Research (1989) 75:245-246.
Rico, et al., "Cyclic Nucleotide Changes Induced in Human Leukocytes by a Product of Axenically Grown Entamoeba Histolytica That Inhibits Human Monocyte Locomotion," Parisitology Research (1995) 81:158-162.
Scherer, et al., "Inhibition of Contact Cutaneous Delayed Hypersensitivity Reactions to DNBc in Guinea Pigs by the Monocyte Locomotion Inhibitory Factor (MLIF) Produced by Axenically Grown Entamoeba Hystolytica," Archives of Medical Research, vol. 28, Suppl., pp. S237-S238, 1997.
McConchie, et al., Infection and Immunity, 2006, vol. 74, p. 6632-6641.
Rahman, et al., PloS Pathogens, 2006, vol. 2, p. 0066-0077.

\* cited by examiner

*Primary Examiner*—Bruce Campell
*Assistant Examiner*—Agnieszka Boesen
(74) *Attorney, Agent, or Firm*—Rissman Hendricks & Oliverio LLP

(57) ABSTRACT

The invention relates to an anti-inflammatory oligopeptide which can be obtained from the microorganism *Entamoeba histolytica* or synthesized by known methods. The oligopeptides are useful in treating inflammatory diseases when formulated in pharmaceutical compositions for administration to patients.

5 Claims, 5 Drawing Sheets

| SEQUENCE | PREDICTED MASS | MALDI/LINEAR MASS | % ERROR |
|---|---|---|---|
| MQCNS + H | 583 | 584 | 0.2 |
| MQCNS + H + Na | 606 | 606 | 0.0 |
| (MQCNS)$_2$ + H | 1164 | 1162 | 0.2 |
| (MQCNS)$_2$ + H + Na | 1187 | 1186 | 0.1 |
| (MQCNS)$_2$ + H + Na + O | 1203 | 1202 | 0.1 |
| MQCNS + H + Iaa* | 641 | 640 | 0.2 |

* IODACETIC ACID (MASS : 58)

Fig. 1

| | AMINO ACIDS (SINGLE LETTER CODE) | | | | | | | | | | | | | | | | | | | | | |
|---|---|---|---|---|---|---|---|---|---|---|---|---|---|---|---|---|---|---|---|---|---|---|
| CYCLE | A | D | E | F | G | H | I | K | L | M | N | P | Q | R | S | SMC | T | V | W | C | nl | nv |
| 1 | 29.55 | 1.65 | 6.58 | 0.00 | 6.24 | 3.40 | 0.67 | 2.53 | 0.82 | 1482.44 | 2.26 | 9.66 | 2.31 | 2.76 | 6.94 | 0.23 | 10.03 | 0.00 | 0.00 | 0.67 | 7.67 | 3.09 |
| 2 | 3.65 | 0.00 | 384.03 | 0.00 | 17.78 | 0.00 | 0.19 | 1.40 | 0.23 | 80.13 | 19.09 | 1.68 | 1374.29 | 1.47 | 2.78 | 0.64 | 0.00 | 0.00 | 0.00 | 0.42 | 0.14 | 1.92 |
| 3 | 4.20 | 0.20 | 21.07 | 3.52 | 1.09 | 21.77 | 0.00 | 27.99 | 0.00 | 8.26 | 3.22 | 6.97 | 1022.25 | 59.02 | 77.74 | 8.93 | 0.00 | 0.00 | 0.00 | 1027.52 | 8.62 | 2.47 |
| 4 | 5.98 | 165.53 | 4.69 | 0.25 | 1.88 | 3.14 | 0.21 | 0.76 | 0.09 | 1.81 | 1252.98 | 0.26 | 18.21 | 10.88 | 26.01 | 0.01 | 0.00 | 0.14 | 0.00 | 39.00 | 0.70 | 1.58 |
| 5 | 30.29 | 0.00 | 1.99 | 4.09 | 0.83 | 23.99 | 0.16 | 1.13 | 0.00 | 1.00 | 224.76 | 0.23 | 0.00 | 97.13 | 1174.19 | 0.00 | 0.00 | 0.11 | 0.00 | 5.30 | 0.32 | 1.71 |
| 6 | 10.41 | 0.00 | 0.82 | 0.87 | 0.61 | 6.98 | 0.12 | 0.00 | 0.17 | 0.69 | 38.15 | 0.09 | 0.00 | 29.07 | 345.06 | 0.17 | 0.00 | 0.10 | 0.00 | 1.25 | 7.09 | 1.78 |
| 7 | 2.32 | 0.00 | 0.39 | 0.42 | 0.39 | 1.64 | 0.10 | 0.00 | 0.12 | 0.50 | 11.25 | 0.03 | 0.00 | 6.32 | 79.86 | 0.09 | 0.00 | 0.11 | 0.00 | 0.41 | 0.41 | 1.71 |
| 8 | 0.59 | 0.00 | 0.27 | 0.10 | 0.33 | 0.47 | 0.12 | 0.07 | 0.16 | 0.40 | 4.38 | 0.05 | 1.12 | 1.68 | 19.23 | 0.05 | 0.00 | 0.09 | 0.00 | 0.17 | 0.04 | 1.60 |
| 9 | 0.27 | 0.00 | 0.19 | 0.09 | 0.35 | 0.20 | 0.05 | 0.06 | 0.16 | 0.35 | 2.25 | 0.04 | 0.78 | 0.79 | 6.25 | 0.04 | 0.00 | 0.08 | 0.00 | 0.17 | 0.07 | 1.58 |
| 10 | 0.19 | 0.00 | 0.16 | 0.09 | 0.25 | 0.00 | 0.06 | 0.07 | 0.14 | 0.30 | 1.59 | 0.04 | 0.56 | 0.58 | 2.89 | 0.02 | 0.00 | 0.05 | 0.00 | 0.13 | 0.05 | 1.62 |
| 11 | 0.18 | 0.42 | 0.13 | 0.08 | 0.30 | 0.04 | 0.08 | 0.00 | 0.18 | 0.28 | 1.22 | 0.03 | 0.47 | 0.52 | 1.91 | 0.05 | 0.00 | 0.07 | 0.00 | 0.15 | 5.09 | 1.60 |
| 12 | 0.17 | 0.00 | 0.14 | 0.18 | 0.29 | 3.01 | 0.12 | 0.08 | 0.16 | 0.27 | 1.03 | 0.03 | 0.42 | 0.27 | 1.53 | 0.09 | 0.00 | 0.09 | 0.00 | 0.14 | 0.44 | 1.63 |
| 13 | 0.16 | 0.00 | 0.13 | 0.10 | 0.30 | 3.02 | 0.12 | 0.00 | 0.16 | 0.24 | 0.81 | 0.05 | 0.35 | 0.43 | 1.27 | 0.10 | 0.00 | 0.08 | 0.00 | 0.09 | 0.07 | 1.67 |
| 14 | 0.16 | 0.00 | 0.12 | 0.07 | 0.32 | 2.51 | 0.16 | 0.00 | 0.20 | 0.23 | 0.71 | 0.02 | 0.36 | 0.32 | 1.10 | 0.05 | 0.00 | 0.09 | 0.00 | 0.18 | 0.04 | 1.61 |
| 15 | 0.17 | 0.00 | 0.11 | 0.08 | 0.31 | 1.74 | 0.14 | 0.00 | 0.16 | 0.21 | 0.64 | 0.06 | 0.32 | 0.47 | 0.99 | 0.06 | 0.03 | 0.06 | 0.00 | 0.15 | 0.03 | 1.59 |

SMC  S-methylated cysteine
nl   norleucine
nv   norvaline

| CYCLE #: | 1 | 2 | 3 | 4 | 5 |
|---|---|---|---|---|---|
| SEQUENCE: | Met | Gln | Cys | Asn | Ser |

Fig. 2

NATIVE MLIF AND CONSTRUCT ACTIVITY (INHIBITION OF *IN VITRO* MP CHEMOTAXIS)

|              | μP/hpf[e]  | % chemotaxis |
|--------------|------------|--------------|
| GEY's - A[f] | 48 ± 12    | -            |
| ZAS[g]       | 102 ± 3    | 100          |
| ZAS + MLIF   | 41 ± 4     | 40           |
| ZAS + AM     | 116 ± 9    | 113          |
| ZAS + CONSTRUCT | 48 ± 4  | 47           |

[a] MONOCYTE LOCOMOTION INHIBITORY FACTOR
[b] MONONUCLEAR PHAGOCYTE
[c] OPSONIZED ZYMOSAN
[d] PHOSPHATE BUFFERED SALINE pH 7.4
[e] HIGH POWER FIELD (400x)
[f] ALBUMIN
[g] ZYMOZAN ACTIVATED SERUM

Fig. 3C

MONOCYTE LOCOMOTION INHIBITORY FACTOR

CROSS REFERENCE TO RELATED APPLICATIONS

This application is a continuation of U.S. application Ser. No. 10/861,123, filed Jun. 4, 2004, which is a continuation-in-part of U.S. application Ser. No. 10/263,947, filed Oct. 3, 2002, now U.S. Pat. No. 7,078,044, which is a continuation of U.S. application Ser. No. 09/342,956, filed Jun. 29, 1999, now U.S. Pat. No. 6,524,591. The pertinent portions of the above-indentified applications and patents are incorporated herein by reference in their entirety.

BACKGROUND OF THE INVENTION

The invention relates to an isolated oligopeptide, obtained from *Entamoeba histolytica*, which is useful in treating inflammatory conditions, such as rheumatoid arthritis and psoriasis. The isolated oligopeptide, which is identified herein as monocyte locomotion inhibitory factor ("MLIF"), is useful for suppressing leukocyte, macrophage and neutrophil activity which may be caused by an inflammatory event.

*Entamoeba histolytica*, in motile form, is a dynamic pleomorphic protozoon which is common in Mexico, Africa and Asia. *E. histolytica* is an invasive parasite having a simple cytoplastic structure. Infection by pathogenic *E. histolytica* may result in the invasion of several organs and tissues in humans. The most commonly affected organs are the colon and the liver. Less frequently, the parasite may invade the lungs, the brain, the skin and the genitalia.

*E. histolytica* is known to cause liver abscesses and other lesions in the human population. In amoebic liver lesions, a moderate inflammation occurs characterized by the presence of neutrophils, epithelioid cells and macrophages, with less abundant neutrophils, lymphocytes and plasma cells. It has been observed that although the early stages of parasitic invasion are characterized by acute inflammation in which even some eosinophilic leukocytes occur, the advanced stages are characterized by a scarcity of inflammation. E Moreover, livers with such hepatic abscesses have been found to regenerate perfectly without a trace of scarring following effective treatment with appropriate medicines. Sepulveda, B. et al., *Immunology of Parasitic Disease*, ppg. 170-191 (1982).

The supernatant fluid of axenically grown *E. histolytica* has been shown to inhibit chemotaxis, chemokinesis and the random mobility of human mononuclear phagocytes. Human polymorphonuclear neutrophil phagocyte locomotion is apparently unaffected. It has been postulated that the inhibition of human mononuclear phagocytes by the entamoeba product contributes to the lack of inflammatory reaction observed in the advanced stages of invasive amoebiasis, and consequently and auspiciously, to the lack of scar tissue formation upon healing of amoebic lesions through regeneration. Kretschmer, R. R. et al., *Parasite Immunology*, 7, Pages 527-543 (1985). See also Rico, G. et al., *Archives of Medical Research*, 28(5), pages 235-236 (1997). This product may also constitute a defensive factor of the amoeba which is capable of reducing or blocking the inflammatory response of the host.

In basic terms, inflammation is a localized, protective response elicited by a foreign antigen, or by an injury or destruction of tissue. Inflammation occurs when tissues are injured by viruses, bacteria, trauma, chemicals, heat, cold, or any other harmful stimuli. In such instances, the classic weapons of the immune system (T cells, B cells, macrophages) interface with cells and soluble products which are mediators of inflammatory responses (neutrophils, eosinophils, basophils, macrophages, cytokines, kinin and coagulation systems, and the complement cascade).

A typical inflammatory response is characterized by (i) migration of leukocytes at the site of the injury or trauma; (ii) specific and nonspecific recognition of foreign antigens indicated by B and T lymphocytes, macrophages and the alternative complement pathway; (iii) amplification complement components, lymphokines and monokines, kinines, arachidonic acid metabolites, and mast cell/basophil products; and (iv) macrophage, neutrophil and lymphocyte participation in antigen destruction, with the ultimate removal of antigen particles or injured tissue by phagocytosis. Diseases associated with such inflammatory responses include rheumatoid arthritis, lupus and psoriasis. The rejection of allografts following organ transplantation also involves these inflammatory responses.

Although inflammation is an essential defense mechanism against infections, it is nevertheless appropriate to consider approaches to modulate or directly inhibit the inflammation if failure to do so would lead to severe and irreversible damage to organs and tissue, including nonfunctional scarring.

It will therefore be readily appreciated that a continuing need exists to develop improved treatments for inflammatory diseases, as well as treatments for conditions of moderate and extreme harmful inflammation.

SUMMARY OF THE INVENTION

It has now been discovered that oligopeptides obtained from the parasite *Entamoeba histolytica* have unique and selective anti-inflammatory characteristics which are useful for treating inflammatory conditions. The oligopeptides have been found to reduce the activity and mobility of leucocytes which are normally activated during an inflammation process in a subject. This oligopeptides are identified by the amino acid sequences set forth in SEQ ID NO:1 and SEQ ID NO:2.

Accordingly, in one important aspect of the invention, compositions are provided comprising the oligopeptide set forth in SEQ ID NO:1.

In one embodiment of this aspect of the invention, the oligopeptide is a homodimer or a heterodimer. The homodimer comprises two oligopeptides as described in SEQ ID NO:1 linked together by, for instance, a cys-cys disulfide bond. A heterodimer comprises two oligopeptides, one of which is the oligopeptide as described in SEQ ID NO:1, which is, in effect, the active part of the heterodimer, and the other component is a different oligopeptide.

In another embodiment of this aspect, the oligopeptide is an analogue of SEQ ID NO:1. This oligopeptide contains a proline in place of the glutamine in the second position, and is set forth in SEQ ID NO:2.

According to another aspect of the invention, a method for treating a subject having a condition characterized by inflammation is provided. The method includes administering to the subject an amount of an oligopeptide, which includes the amino acid sequences of SEQ ID NO:1 and SEQ ID NO:2, effective to reduce the inflammation in the subject. Inflammatory conditions which may be treated in this way include rheumatoid arthritis, lupus and psoriasis.

This aspect of the invention also includes suppression allograft rejection following organ transplantation.

This aspect of the invention also includes the inhibition of leukocyte activity and mobility to prevent the occurrence of scarring in a patient. The oligopeptide is administered to the patient prior to the onset of the scarring process in the body or during healing.

In certain embodiments, the oligopeptide is administered to the subject as a treatment after the inflammatory condition has developed. In other embodiments, the compositions of this invention are formulated into pharmaceutical preparations to prevent the onset of the inflammatory condition, or, in another embodiment, as an anti-amoebic vaccine for immunization against amoebic invasion.

According to still another aspect of the invention, a pharmaceutical composition is provided. The pharmaceutical composition includes all isolated oligopeptide which comprises the amino acid sequences set forth in SEQ ID NO:1 or SEQ ID NO:2, and a pharmaceutically acceptable carrier. The pharmaceutical composition also can include a compound which facilitates transport of the oligopeptide to the site of the inflammation. The pharmaceutical composition can be formulated into a product which can either be used for treatment or as a vaccine. The composition can include additives, excipients and adjuvants appropriate for treatment products or vaccines.

According to another aspect of the invention, nucleic acid sequences are provided. The nucleic acid sequences encode the oligopeptides identified in SEQ ID NO:1 and SEQ ID NO:2. Also included in the invention are vectors, such as expression vectors, which include the foregoing nucleic acid sequences. The nucleic acids can be used for medicinal applications, such as gene therapy applications.

In yet another aspect of the invention, oligopeptide-based compositions are provided for administration to a subject to prevent scarring which is the result of an inflammatory process mediated by leukocytes. Recruitment of fibroblasts, which are integral to the scarring process, is dependent on leukocyte macrophages. The activity and mobility of leukocyte macrophages is effectively blocked by the oligopeptide-based compositions of this invention.

The use of the foregoing compositions, isolated oligopeptides and isolated nucleic acids in the preparation of various medicaments is also provided.

These and other aspects of the invention are described in greater detail below.

BRIEF DESCRIPTION OF THE DRAWINGS

FIG. 1 is a table summarizing the results of a mass spectrometry ("MS") analysis of a sample of monocyte locomotion inhibitory factor ("MLIF").

FIG. 2 is a table showing the amino acid sequence structure of MLIF using Edman-N degradation sequencing.

FIG. 3C is a table comparing the activity of native MLIF and a synthetic MLIF peptide for the in vitro inhibition of peripheral blood macrophage chemotaxis.

DETAILED DESCRIPTION OF THE INVENTION

Figure 3A:
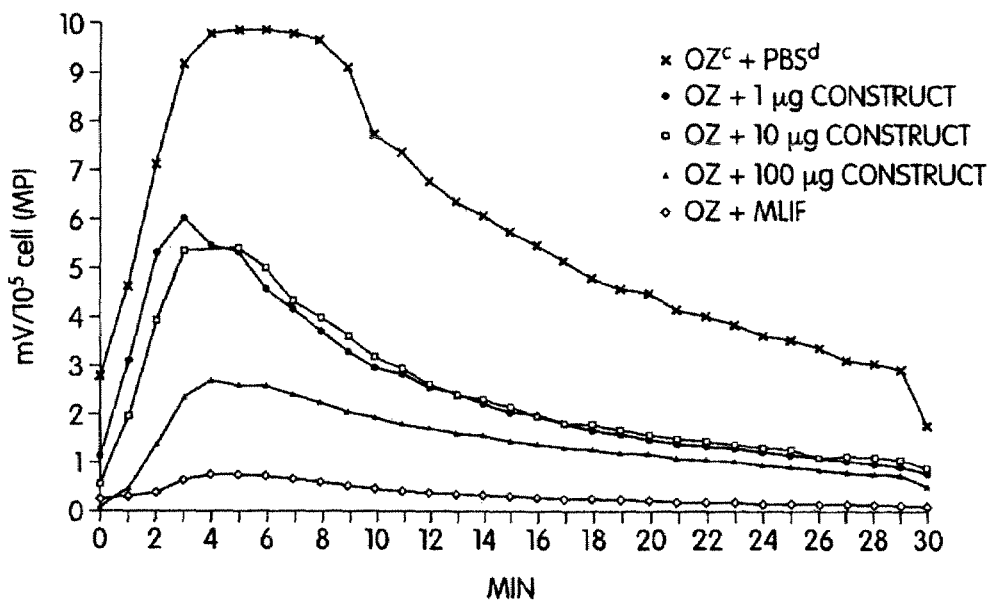
FIG. 3A is a diagram comparing the activity of native MLIF and a synthetic MLIF peptide in inhibiting the repiratroy burst of human peripheral blood macrophage cells ("MP").

The invention relates to compositions comprising oligopeptides which are capable of reducing the effects of inflammation in a subject due to an inflammatory condition, such as conditions resulting from rheumatoid arthritis or organ transplantation, when administered before, during and/or after the inflammatory event. Thus, administration of the compositions of the invention selectively inhibits the activity and mobility of certain leukocytes, i.e., monocytes, and also inhibits the metabolism of both monocytes and neutrophils, in the vicinity of the inflammation, without affecting these functions in other cells, i.e., eosinophils.

As used herein, the expression "monocyte locomotion inhibitory factor" (MLIF) means the oligopeptide isolated from the supernatant fluid of axenically grown *E. histolytica*, including the isolated oligopeptide of SEQ ID NO:1. MLIF also includes oligopeptide analogues of SEQ ID NO:1 having the same activity as SEQ ID NO:1, such as the oligopeptides of SEQ ID NO:2.

Also as used herein, an "isolated" peptide means a peptide described herein that is not in its natural state (e.g., it is dissociated from a larger protein molecule in which it naturally occurs), or it is a non-naturally occurring fragment of a naturally occurring protein, or it is dissociated from other cell components with which is associated in its natural state. Isolated also may mean that the amino acid sequence of the peptide does not occur in nature, for example, because the sequence is modified from a naturally occurring sequence, or because the sequence does not contain flanking amino acids which are present in nature.

An isolated peptide can be purified from a biological extract, prepared in vitro by recombinant or synthetic means, and/or modified by attachment of a moiety (e.g., a fluorescent, radioactive, or enzymatic label, or an unrelated sequence of amino acids to make a fusion protein) which does not correspond to a portion of the peptide in its native state. Isolated peptides include chimeric proteins comprising a fusion of an isolated peptide with another peptide, e.g., a peptide capable of targeting the isolated peptide to a cell type or tissue type, enhancing stability of the isolated peptide under assay conditions, or providing a detectable moiety, such as green fluorescent protein. A moiety fused to an isolated peptide or a fragment thereof also may provide means of readily detecting the fusion protein, e.g., by immunological recognition or by fluorescent labeling. Purified isolated peptides include peptides isolated by methods including, but not limited to, immunochromotography, HPLC, size-exclusion chromatography, ion-exchange chromatography and immune-affinity chromatography.

Likewise, "isolated" as used in connection with nucleic acids which encode peptides embraces all of the foregoing, e.g., the isolated nucleic acids are dissociated from adjacent nucleotides with which they are associated in nature, and can be produced recombinantly, synthetically, by purification from biological extracts, and the like. Isolated nucleic acids can contain a portion which encodes for one of the foregoing peptides and another portion which codes for another peptide or protein.

The isolated nucleic acids also can be labeled. Preferably the nucleic acids include codons which are preferred for mammalian usage. In certain embodiments, the isolated nucleic acid is a vector, such as an expression vector, which includes a nucleic acid which encodes one of the foregoing isolated peptides.

The oligopeptides of this invention have been isolated from a culture medium containing the parasitic amoeba *Entamoeba histolytica*. It has been discovered that axenic cultures of *E. histoytica* inhibit locomotion of leukocytes when compared to a virgin axenic control medium. Surprisingly, it has been found that the amoeba does not destroy factors that stimulate locomotion in virgin axenic media. Rather, the amoeba produces de novo a substance that inhibits leukocyte locomotion, and leukocyte function involving reactive oxygen intermediates ("ROI"), such as $H_2O_2$, and reactive nitrogen intermediates ("RNI"), such as NO. This substance has been identified as a heat stable peptide having a molecular weight of about 583 Daltons. The amino acid sequence of the peptide is shown in SEQ ID NO:1. Using single letter amino acid abbreviations, the oligopeptide is represented as:

SEQ ID NO:1    M - Q - C - N - S

The oligopeptide of SEQ ID NO:1 is specific for mononuclear phagocytes (monocytes) and neutrophil polymorphonuclear leukocytes, but does not affect other cells, such as eosinophils. Moreover, the oligopeptide interacts with human mononuclear phagocytes through a receptor on the phagocytes, and as a result generates an increase in the cytoplasmic mediator cyclic AMP. This indicates that the oligopeptide is a highly selective factor inhibiting the locomotion and metabolic production of ROI and RNI of mononuclear leukocytes, and the metabolism of polymorphonuclear neutrophils, without affecting either the locomotion or metabolism of polymorphonuclear eosinophils.

Two of the molecular effects of the oligopeptide upon human leukocytes, i.e., the depression of reactive oxygen intermediates, and the increase in cytoplasmic cAMP, are known to attenuate the activation of the transcription factors NF-κB and AP-1, which are required for the coordinate expression of TNF-α, IL-1β and IL-6 genes, and possibly other factors which are ingredients of the inflammatory reaction. This is further evidence that the oligopeptide of this invention is useful as an anti-inflammatory agent, or as a protective immunogen.

The oligopeptide of SEQ ID NO:1 has a molecular weight of about 583 Daltons, and is heat stable to incubation at 56° C. and storable at −70° C. It has been observed that the oligopeptide forms dimers by means of disulfide bridges. A synthetic peptide of SEQ ID NO:1 having a purity of 96% and a mass of 581.6 Daltons, has also been constructed and found to have the same anti-leukocyte properties as the native oligopeptide.

This invention is not limited to one specific oligopeptide, and it encompasses other preferred, isolated oligopeptides which vary from the foregoing sequences by the addition of amino acid residues at one or both ends of the oligopeptide.

The amino acid sequence of the oligopeptides may be of natural or non-natural origin, that is, it may comprise a natural peptide molecule that is a piece of a naturally occurring molecule, it may comprise a sequence modified from a naturally occurring molecule, or it may be entirely synthetic so long as the peptide has the ability to reduce inflammation and retard leukocyte activity. The peptides of the invention also may be altered versions of the foregoing. For example, peptides in this context may be fusion proteins of the oligopeptide and unrelated amino acid sequences, synthetic peptides of amino acid sequence shown in SEQ ID NO:1, labeled peptides, peptides coupled to nonpeptide molecules (for example in certain drug delivery systems), and other molecules which include the amino acid sequence of SEQ ID NO:1, or a biologically active analogue thereof.

Nonpeptide analogues of peptides, e.g., those which provide a more stabilized structure, or altered biodegradation, or which can act at lower concentrations, are also contemplated. Peptide mimetic analogues can be prepared based on a selected peptide by replacement of one or more residues by nonpeptide moieties. Preferably, the nonpeptide moieties permit the peptide to retain its natural conformation, or stabilize a preferred conformation. One example of methods for preparing nonpeptide mimetic analogues from peptides is described in Nachman et al., *Regul. Pept.* 57:359-370 (1995). The term "peptide" or "oligopeptide," as used herein, embraces all of the foregoing, and also includes biologically active variants of the foregoing.

Likewise, various changes may be made to the oligopeptide including the addition of various side groups which do not affect the manner in which the oligopeptide functions, or which favorably affect the manner in which the oligopeptide functions. Such changes may involve adding or subtracting charge groups, substituting amino acids, adding lipophilic moieties that do not affect biological activity but that affect the overall charge characteristics of the molecule facilitating drug delivery, etc. For each such change, no more than routine experimentation is required to test whether the molecule functions according to the invention. One simply makes the desired change or selects the desired peptide and evaluates the peptide for anti-inflammatory function as described in detail in the examples.

Both homodimers and heterodimers of SEQ ID NO:1, described above, and SEQ ID NO:2, described below, are also included within the scope of this invention. The homodimers of this invention comprise two oligopeptides joined together by a cys-cys disulfide bond. The heterodimers of this invention comprise the oligopeptide of SEQ ID NO:1 or SEQ ID NO:2 joined to another peptide, which may an oligopeptide of this invention, or a small molecule, or a chemical entity, the only requirement being that the heterodimer should retain the biological activity of the oligopeptides of this invention. The oligopeptide of this invention can be bonded to the other peptide or small molecule with a disulfide bond, one or more peptide bonds, or another chemical linkage. The heterodimer can also include the oligopeptide of SEQ ID NO:1 joined to the oligopeptide of SEQ ID NO:2.

The invention also embraces functional variants of the oligopeptide. As used herein, a "functional variant" or "variant" of an isolated peptide is a peptide which contains one or more modifications to the primary amino acid sequence of the peptide and retains the properties disclosed herein. Modifications which create a functional variant of the peptide can be made, for example, 1) to enhance a property of a peptide, such as peptide stability in an expression system; 2) to provide a novel activity or property to the peptide, such as addition of an antigenic epitope or addition of a detectable moiety; or 3) to provide a different amino acid sequence that produces the same or similar peptide properties. Modifications to a peptide can be made to a nucleic acid which encodes the peptide, and can include deletions, point mutations, truncations, amino acid substitutions and additions of amino acids. Alternatively, modifications can be made directly to the peptide, such as by cleavage, addition of a linker molecule, addition of a detectable moiety, such as biotin, addition of a fatty acid, substitution of one amino acid for another and the like. Modifications also embrace fusion proteins comprising all or part of the oligopeptide amino acid sequence.

If a variant involves a change to an amino acid of SEQ ID NO:1, then functional variants of the oligopeptide can have either conservative or non-conservative amino acid substitutions. Conservative amino acid substitutions are substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Other methods for identifying functional variants of the oligopeptide are provided in a published PCT application of Strominger and Wucherpfennig (US/96/03182). These methods rely upon the development of amino acid sequence motifs to which potential epitopes may be compared. Each motif describes a finite set of amino acid sequences in which the residues at each (relative) position may be (a) restricted to a single residue, (b) allowed to vary among a restricted set of residues, or (c) allowed to vary among all possible residues.

Thus, methods for identifying functional variants of a peptide are provided. In general, the methods include selecting a peptide, such as the oligopeptide comprising the amino acid sequence of SEQ ID NO:1. A first amino acid residue of the peptide is mutated to prepare a variant peptide. In one embodiment, the amino acid residue can be mutated according to the principles set forth in the Strominger and Wucherpfennig PCT application described above. In other embodiments, mutation of the first amino acid residue can be selected and tested using computer models of peptide conformation. Any method for preparing variant peptides can be employed, such as synthesis of the variant peptide, recombinantly producing the variant peptide using a mutated nucleic acid molecule, and the like. The properties of the variant peptide in relation to the oligopeptides described previously are then determined according to standard procedures as described herein.

One such specific variant involves the substitution of proline (P) in place of glutamine (Q) in position number 2. This oligopeptide is shown in SEQ ID NO:2:

```
        SEQ ID NO:2          M-P-C-N-S
```

The codons encoding glutamine, namely CAA and CAG, are similar to two of the codons encoding proline, namely CCA and CCG. Thus, a single substitution (C for A) of the middle nucleotide results in a different amino acid being encoded.

Peptide variants may also be generated by randomizing the amino acid at one of the positions in the oligopeptide using non-conservative substitutions. In this manner, a synthetic oligopeptide could be generated by, for instance, randomizing the amino acid at one of positions 1 through 5 of the oligopeptide, and testing the resulting synthetic molecule for function or biochemical activity in a suitable assay as described below. For instance, SEQ ID NO:2 can be more broadly described as MXCNS, where X is any residue other than glutamine or proline, including residues of amino acids that do not occur naturally in proteins. Further, an amino acid can be replaced by a different chemical entity provided the new entity is capable of forming the necessary covalent linkages with the other amino acids in the chain.

Peptides useful in the invention can be linear, circular or cyclized by natural or synthetic means. For example, disulfide bonds between cysteine residues may cyclize a peptide sequence. Bifunctional reagents can be used to provide a linkage between two or more amino acids of a peptide. Other methods for cyclization of peptides, such as those described by Anwer et al. (*Int. J. Pep. Protein Res.* 36:392-399, 1990) and Rivera-Baeza et al. (*Neuropeptides* 30:327-333, 1996) are also known to those of skill in the art.

The peptides described herein are characterized by their ability to reduce or eliminate the effects of inflammation. Although not wishing to be bound by any particular mechanism of operation, it is believed that the peptides may exert their anti-inflammatory effects by one or more of the following mechanisms (among others): the elevation of intracellular cyclic AMP, the inhibition of leukocyte locomotion due to the inflammatory event, or the regulation of transcription factors such as NF-κB and AP-1. These properties provide a basis for making and testing variant peptides.

Other methods for testing peptide function involve the use of cells containing a functional MLIF receptor for the peptide. Suitable cell lines include human monocytes, such as the human monocyte cell line U937, and human neutrophils. Other suitable cell lines can be identified with minimal experimentation, such as by contacting the cells with the oligopeptide of SEQ ID NO:1, and determining whether the intracellular level of cyclic AMP is increased. For instance, a candidate cell line is provided and, for certain assays such as the assay described in Example 2, an independent stimulus is also provided (in the case of monocyte/macrophage cells, for example, this stimulus can consist of opsonized zymosan particles, or formyl-Met-Leu-Phe peptide). Alternatively, the MLIF receptor protein can be identified by screening a collection of orphan receptors by, for example, expressing their cDNA in a cell line that does not have an MLIF receptor, and testing whether the orphan receptor confers sensitivity (measured, for instance, as increased cyclic AMP) to MLIF or an MLIF analogue.

Once a cell bearing the MLIF receptor, or the receptor protein, is identified, the function tests outlined previously can be readily performed. In addition, MLIF agonists and antagonists can also be identified using well known techniques. To conduct an assay for agonist activity, the effect of a candidate agent on a biological or biochemical measurement indicative of cell activation through the MLIF receptor can be evaluated. Any characteristic of the cellular response to MLIF or its biologically active analogue s can be evaluated, such as the inhibition of specific binding of a labelled MLIF analogue to the cell, an increase in cyclic AMP, phosphorylation of a protein kinase A substrate, or inhibition of the oxidative burst of monocytes or neutrophils monitored by the production of ROI.

For some embodiments of the agonist assay, including competition with a labelled MLIF analogue for specific binding to the cells, it will be clear from the primary assay itself that compounds producing a positive result act at the site of the MLIF receptor. Such compounds can be classified as either agonists or antagonists, for instance by examining the ability of the individual compounds to produce an increase in cyclic AMP in the cells.

Other embodiments which provide an efficient procedure for discovering agonists may nonetheless also detect compounds acting through other receptors to produce the desired effect, such as an increase in cyclic AMP. These compounds will have no value as MLIF agonists, and in many cases they will bind to receptors for which effective agonists and antagonists are already available (β-adrenergic receptors), or such compounds may have widespread expression, rather than being limited to a few cell types, and therefore of limited interest as pharmaceutical lead compounds. A further feature of an assay for an MLIF agonist is thus the determination of whether a compound that appears to be an effective agonist is actually acting through the MLIF receptor, or whether it is acting through another receptor but producing the same effect. This determination can be made by assessing whether the effects of the candidate agonist and MLIF are additive, and whether there is cross-desensitization between the candidate agonist and MLIF. For example, the proposed agonist can be tested in a competitive binding assay with labelled MLIF, or by standard pharmacological tests known to those skilled in the art.

In one embodiment, the candidate agonist compounds include the MLIF peptide, or a biologically active analogue thereof, as part of the structure of the agonist. These compounds can have elements of a library, such as a random peptide library or a combinatorial chemical library, or the compounds can be formed by covalently linking the MLIF peptide, or MLIF analogue, to another peptide or chemical entity.

To conduct an assay for antagonist activity, MLIF, or an MLIF analogue, is used to elicit a biological or biochemical response, and the ability of the candidate antagonist to reduce or prevent the response to MLIF is monitored. The assay can be carried out by contacting a responsive cell with the candidate antagonist and MLIF, or a biologically active analogue thereof, and making a biological or biochemical measurement indicative of activation through the MLIF receptor. Suitable measurements include, by way of example, the inhibition of specific binding of a labelled MLIF analogue to the cell, an increase in cyclic AMP, phosphorylation of a protein kinase A substrate, or the oxidative burst of monocytes or neutrophils monitored by the production of ROI. Preferred antagonist candidates include the MLIF peptide, or a biologically active analogue thereof, as part of the structure of the antagonist with elements of a random peptide library or a combinatorial chemical library, or the antagonist candidate can be formed by covalently linking the MLIF peptide, or MLIF analogue, to another peptide or chemical entity.

This invention also includes a library of compounds which are targeted to the MLIF receptor, and a high-throughput screening assay which can be used to identify a candidate agent which has an affinity for the MLIF receptor.

Accordingly, a library of potentially active compounds is prepared. The library is constructed to include compounds which are targeted to the MLIF receptor to improve the possibility that screening of the library will result in the identification of biologically active compounds, such as MLIF agonists and antagonists. In a preferred embodiment, the library can incorporate an MLIF peptide, such as the peptide of SEQ ID NO:1, or a biologically active analogue, in the structure of at least some of the compounds in the library. Compounds which incorporate the MLIF peptide as part of the structure of the compound can have the peptide covalently linked to another moiety which can be structurally diverse from the MLIF peptide. For instance, the library of compounds can contain components from random peptide libraries, combinatorial chemical libraries, or compounds covalently linked to the MLIF peptide or an MLIF peptide analogue, or mixtures of such components. Thus, in addition to containing compounds which contain the MLIF peptide or its analogue as a common structural feature, biologically active MLIF analogue s can also be included as part of the structure of such compounds. Moreover, the covalent linkage of the MLIF portion to another portion of a molecule can differ from one compound to another. Further, since the structural requirements for targeting by the MLIF portion of a heterodimer and for agonist activity of a homodimer may not be identical, the library can also include compounds where the MLIF-like portion of some or all of the compounds is chosen due to its structural similarity to MLIF or its analogues, without regard to the biological activity of its homodimer.

The compounds in the library can be screened for MLIF activity in a high-throughput screening assay to identity a target compound which acts at the MLIF receptor using conventional techniques. Candidate agonist or antagonist compounds, cells which include the MLIF receptor, and in some cases MLIF or a biologically active analogue, or an independent stimulus, such as opsonized zymosan particles, are provided as components in such an assay. A biological or biochemical change characteristic of the response to MLIF is measured, and the measurement for a sample in the presence of a target compound (or a mixture of target compounds) is assessed relative to the measurement for samples without the addition of the candidate compounds, or with control additions.

Such a high-throughput screening assay can he conducted using, for instance, 96 well plates for containing samples subject to analysis using the basic methods described above, but incorporating high speed screening techniques. These methods involve automated execution in a multiwell format in which many of the steps are controlled by computer and carried out by robotic equipment. Other formats, such as the use of synthetic chemical libraries affixed to a solid support and available for release into microdroplets, can also be used to advantage. These high-throughput screening methods can be used screen large libraries of candidate agents, including natural product libraries, organic chemical libraries, combinatorial chemical libraries, peptide libraries, and modified peptide libraries which incorporate D-amino acids, unconventional amino acids, or N-substituted amino acids at one or more positions. Preferably, the libraries are in a form compatible with screening in multiwell plates.

The peptides of this invention can also be used to generate antibodies useful in diagnostic assays for inflammatory diseases and infection by *E. histolytica* or other microorganisms. The antibodies can be generated using techniques which are well known to those skilled in the art. Such antibodies can be polyclonal or monoclonal, and can comprise murine antibodies, humanized antibodies, or antibody fragments, i.e., FAB fragments.

Further embodiments of this invention include nucleic acid sequences which code for an oligopeptide as described above, or a variant thereof having similar biological activity.

Vectors, including expression vectors, which include the foregoing nucleic acids also are included in the invention. One of ordinary skill in the art is familiar with a variety of cloning and expression vectors, as well as methods for inserting a nucleic acid in a vector, and particularly for operably linking a nucleic acid with a promoter sequence without introducing stop codons, frame shifts or other mutations, to provide efficient expression of the encoded peptide in an expression vector.

Compositions including the oligopeptides having the sequences set forth in SEQ ID NO:1 and SEQ ID NO:2 are administered to a subject to treat a condition characterized by inflammation or by excessive activation of macrophage or neutrophils. Such conditions include rheumatoid arthritis, lupus and psoriasis. Peptides are administered to a subject in need of such treatment in an amount effective to reduce the effects of the inflammation. Such compositions can also be administered to prevent scarring which is the result of a process mediated by leukocytes, the activity and mobility of which are inhibited by the composition. For instance, the recruitment of fibroblasts, which are integral to the scarring process, is dependent on leukocyte macrophages whose activity would be blocked by the oligopeptide-based composition.

Macrophages are also implicated in atherosclerosis, certain neurological diseases, and responses to nerve injuries. Similarly, neutrophils have also been implicated in various diseases. Treatment of such conditions with MLIF, or an MLIF analogue, could have beneficial medical results.

Peptides or other anti-inflammatory compounds may be administered as part of a pharmaceutical composition. Such a pharmaceutical composition may include the peptides in combination with any standard pharmaceutically acceptable carriers which are known in the art. The compositions should be sterile and contain a therapeutically effective amount of the peptides or other therapeutic compound in a unit of weight or volume suitable for administration to a patient. The term "pharmaceutically acceptable" means a non-toxic material that does not interfere with the effectiveness of the biological activity of the active ingredients. The characteristics of the carrier will depend on the route of administration. Pharmaceutically acceptable carriers include diluents, fillers, salts, buffers, stabilizers, solubilizers, and other materials which are well known in the art.

The pharmaceutical compositions of this invention can also include other active ingredients, such as phosphodiesterase IV inhibitors, which would be expected to potentiate an increase in intracellular cyclic AMP.

When used therapeutically, the compounds of the invention are administered in therapeutically effective amounts. In general, a therapeutically effective amount means that amount necessary to delay the onset of, inhibit the progression of, or halt altogether the particular condition being treated. Therapeutically effective amounts specifically will be those which desirably have an effect on the inflammation, or influence the mobility of leukocytes following an inflammatory event. Generally, a therapeutically effective amount will vary with the subject's age, and condition, as well as the nature and extent of the disease in the subject, all of which can be determined by one of ordinary skill in the art. The dosage may be adjusted by the individual physician, particularly in the event of any complication. A therapeutically effective amount typically varies from 0.01 mg/kg to about 1000 mg/kg, preferably from about 0.1 mg/kg to about 200 mg/kg and most preferably from about 0.2 mg/kg to about 20 mg/kg, in one or more dose administrations daily, for one or more days. The effect of the administered therapeutic composition can he monitored by standard diagnostic procedures.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, xylitol, dextrose and sodium chloride, lactated Ringer's or fixed oils. Intravenous vehicles include fluid and nutrient replenishers, electrolyte replenishers (such as those based on Ringer's dextrose or xylitol), and the like. Preservatives and other additives may also be present such as, for example, antimicrobials, antioxidant, chelating agents, and inert gases and the like.

The therapeutics of the invention can be administered by any conventional route, including injection, gradual infusion over time, or oral administration in solid dosage or encapsulated forms. The administration may, for example, be oral, intravenous, intracranial, intraperitoneal, intramuscular, intracavity, intrarespiratory, ocular, oral washes, subcutaneous, or transdermal. The route of administration will depend on the composition of a particular therapeutic preparation of the invention, and in some cases, on the intended site of action. The present compositions can be delivered directly to the site of action.

Other delivery systems can include time-release, delayed release or sustained release delivery systems. Such systems can avoid repeated administrations of the active compounds of the invention, increasing convenience to the subject and the physician. Many types of delayed release delivery systems are available and known to those of ordinary skill in the art. They include polymer-based systems such as polylactic and polyglycolic acid, polyanhydrides and polycaprolactone; nonpolymer systems include lipids such as sterols, and particularly cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, pump-based hardware delivery systems can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

The invention also includes cell implants for secreting the MLIF peptide or analogue to a site in the body. The cell implant includes the vectors described herein for producing a biologically active peptide. Cell implants can be used effectively for treating inflammatory conditions or for preventing scarring.

In addition, the peptides and nucleic acids of this invention can be formulated into vaccines, for preventing invasive amoebiasis, and gene therapy medicines using techniques and formulations which are well know in the art.

EXAMPLES

Experimental Methods (a) Production and isolation of MLIF. The supernatant fluid of mid-log phase axenic cultures of *E. histolytica* HMI-IMSS were obtained and processed by centrifugation and stepwise ultrafiltration using Amicon™ PM50, 30, 10, UM-2 and YCO5 filters (Amicon Corp.), followed by Sephadex™ G-15 (Pharmacia) gel sieve chromatography. MLIF activity (assayed either by inhibition of human peripheral blood macrophage cell (MP) locomotion, or of MP or neutrophil respiratory burst ROI production) is recovered in the 478-735 Dalton fraction. For some experiments MLIF was purified further through a Sepharose™ (Pharmacia) mannan absorption-elution column. Virgin axenic medium treated in the same way was used as a control (b) Preparation of cells. MP (95±2%) and neutrophils (95±2%) were obtained from the peripheral blood of fasting, non-smoking individual donors, using Ficoll-Paque centrifugation and further enrichment of MP by nylon wool adherence. Cell viability was established ($\geqq$94%) before and after the experiments by trypan blue dye exclusion.

(c) MLIF activity. In vitro MLIF activity was assessed either by the inhibition of MP chemotaxis towards zymosan (Sigma) activated serum in double-filter (upper filter 5.0 μm pore size (Nuclepore), lower cell-impermeable filter 8.0 μm pore size (Sartorius)) Boyden chambers, or by the inhibition of MP or neutrophil, Luminol™ (Eastman Kodak) enhanced chemiluminescence after opsonized zymosan particle ingestion, measured in Biorbit 1250 chemiluminometer (LKB) (n>6). In vivo MLIF activity was measured by its capacity to inhibit DNCB (1-chloro-2-4 dinitrobenzene) contact hypersensitivity reactions in individually-caged Harley short hair adult guinea pigs previously (14 days) sensitized with a vesicant DNCB dose (10 mg/ml acetone olive oil (4:1) soaked 5 mm diameter Whatman #2 filter paper disks). Intradermal injections of 0.05 ml of either native MLIF (8 µg/ml), MLIF custom construct (0.001-100 µg/ml), or pyrogen free phosphate buffered saline pH 7.4, were applied just beneath and simultaneous to the application of the eliciting dose of DNCB (0.05 mg/ml soaked paper disks). Disks were removed after 24 h, and redness-induration measured blindly a day later. Biopsies were obtained for histological evaluation in selected samples. The animals were not sacrificed.

(d) Peptide Identification

HPLC: Ultrapac™ RP-HPLC-C18, 5µ (Hewlett Packard) using 90% $H_2O$, 8% TFA and 2% methanol, pH 7.4 for isochratic elution at 0.8 ml/min flow for isolation of native MLIF, or a Vydac™ RP-HPLC-C18 5µ (The Separations Group), using 0.1% TFA in $H_2O$ (Buffer A) and 0.1% TFA in 100% acetonitrile (Buffer B) for isochratic elution at 1.5 ml/min flow for analysis of the MLIF custom construct, were employed, monitoring absorbance at 280 and at 215 nm, respectively. Peptide content of MLIF samples (native and custom construct) was measured by Bio-Rad™ or by Lowry's analysis.

Mass Spectrometry: Because the lower limit of the initially attempted (3 µl of ~8 µg/100 µl 70% formic acid) mass detection by LDMS (laser desorption mass spectrometry) is about 700 Da, and furthermore since no mass was obtained by electrospray mass spectrometry, a 3 µl MLIF sample (~4 µg/12.5 ml 50% $CH_3$ CN/0.05% TFA) was run in MALDI-MS (matrix assisted laser desorption/ionization mass spectrometry). Since the PSD (post source decay) sequencing of two (606.33 and 1186.34 Da) of the five non-matrix related species that were obtained yielded poor results, 0.2 µl and 0.5 µl samples of HPLC purified and reconstituted MLIF (~4 µg/100 µl 50% $CH_3$ CN/0.05% TFA) were applied to a MS/MS (TSQ-LC-MS) system capable of sequencing very small amounts of any and all species present, regardless of whether or not they possess blocked N-termini. Reduction/carboxamidomethylation of the cysteine residue was performed (and residual function of MLIF assessed by the inhibition of MP chemotaxis assay). Finally, Edman-N terminal degradation sequencing (15 cycles) was performed loading into Procise about 1 µg of HPLC-purified MLIF dissolved in 20 µl 50% $CH_3$ CN/0.05% TFA for confirmation of the amino acid sequence. A 96% pure MLIF construct (MQCNS) possessing a single major peak in RP-HPLC-Vydac C18 5µ and a mass of 581.6 by laser molecular ion chromatography, was obtained by custom synthesis (American Peptide Corp.).

(e) Amebic MLIF synthesis. $5 \times 10^6$ E. histolytica HMI-IMSS grown to mid-log phase in 35 ml of complete axenic medium were thoroughly washed and resuspended in cysteine-free axenic medium for 8 h before receiving a 200 µCi pulse of $^{35}$S-cysteine-methionine (Tran-$^{35}$S-label™) (Sigma) for additional 16 h incubation at 37° C., 5% $CO_2$ and constant humidity. The amebas were then washed twice with complete axenic medium and were resuspended in the same medium for 24, 48 and 72 h of additional incubation. Virgin axenic medium treated under the same conditions acted as control. Supernatant fluid of these cultures were obtained through centrifugation and step-wise ultrafiltration, and were chromatographed in a Sephadex-G15 (Pharmacia) ascending flow column and the eluate monitored in a liquid scintillation counter for $^{35}$S-incorporation (Beckman T-6000) and at 280 nM absorbance for peptide identification. The 478-765 Dalton peak at 72 h incubation was tested for MLIF activity (inhibition of chemiluminescence in opsonized zymosan challenged MP); and was loaded into a RP-HPLC-C18 column, with eluate monitoring by 280 nM absorbance and by liquid scintillation for $^{35}$S incorporation.

(f) Statistical analysis. Results of in vitro MLIF activity were analyzed by non-parametric Mann-Whitney or Kruskall-Wallis analysis of variance test, and in vivo activity results by Student's t and Fisher's exact tests.

Example 1

Characterization of MLIF

A 3 µl sample (~4 µg/12.5 ml) of MLIF, run through a matrix assisted laser desorption/ionization mass spectrometry (MALDI-MS), revealed five major m/z species (i.e., 583.75, 606.33, 1162.17, 1186.34 and 1201.58) that were clearly non-matrix associated and all intimately related. Post source decay (PSD) was attempted on the two larger species (i.e., 606.33 and 1186.34) but was unsuccessful. Therefore 0.2 µl and 0.5 µl samples (~4 µg/100 ml) were applied to a MS/MS (TSQ LC-MS) system, yielding a variety of compounds: a major UV absorbing peak with a mass of about 1161, but also one with a mass of about 581. Further application of material disclosed a number of peaks, most of them with a mass of around 1161. The 1161 species appeared to be a single charged ion, the multiple elution of the seemingly same mass could be attributed to multimerization phenomena, the 1161 species being the dimer of the 582 species, possibly formed by disulfide bridges, by non-covalent interactions, or by both. The mass of 606 is the sodium addict of the 583 species; the sodium addict of the 1163 species being the 1184 peak, that generates fragments of doubly charged 582 ions.

Reduction and alkylation using iodoacetic acid, converted the higher mass species of 1162 to a species with a mass of 640, exactly what one would expect for carboxymethylated MQCNS peptide, a single charged ion, which fragmented well, and on MS/MS spectra revealed the sequence MQCNS, the carboxymethylated (reduced-alkylated) cysteine (C*) resulting from the addiction of 58 mass units of the iodoacetic acid (Iaa) to the 581 double charged ion.

FIG. 1 shows that the five molecular species are intimately related, the result of multimerization, stable on the reverse phase, but falling apart into dimers (and monomers) in the electro-spray-ionization (ESI). The small differences in predicted vs. obtained masses are the result of H, Na and O addition. The 1162 species is the mass (MH+) of the dimer from MQCNS, with a disulfide bridge. The addition of Na in turn yields the MH+ of the 1186 species. The double charged ion emerging from the 1162 species is the 584 species; reduction-alkylation using iodoacetic acid adds 58 mass units to the 584 monomer, and a MH+ of the 640 species is now observed by ion trap mass spectrometry. A met-oxidized version of a disulfide linked Na addict dimer would result in the 1202 species. A peptide analogue with an amino acid sequence of MQCNS would have a mass of 581.

The primary structure of MLIF as confirmed by 15 cycles of Edman-N degradation sequencing is shown in FIG. 2.

Initial sequencing yielded 1482 pmoles. The cysteine ispresent in cycle 3, and was observed by a dehydroalanine peak which migrates on PTH-Arg, and a characteristic cysteine degradation peak observed on Tyr, as cysteine cannot be directly identified unless it is modified in some manner. SMC: S-methylated cysteine, nl: nor-leucine, nv: nor-valine.

Example 2

In Vitro Activity of Native MLIF and a Synthetic Construct

Figure 3B:
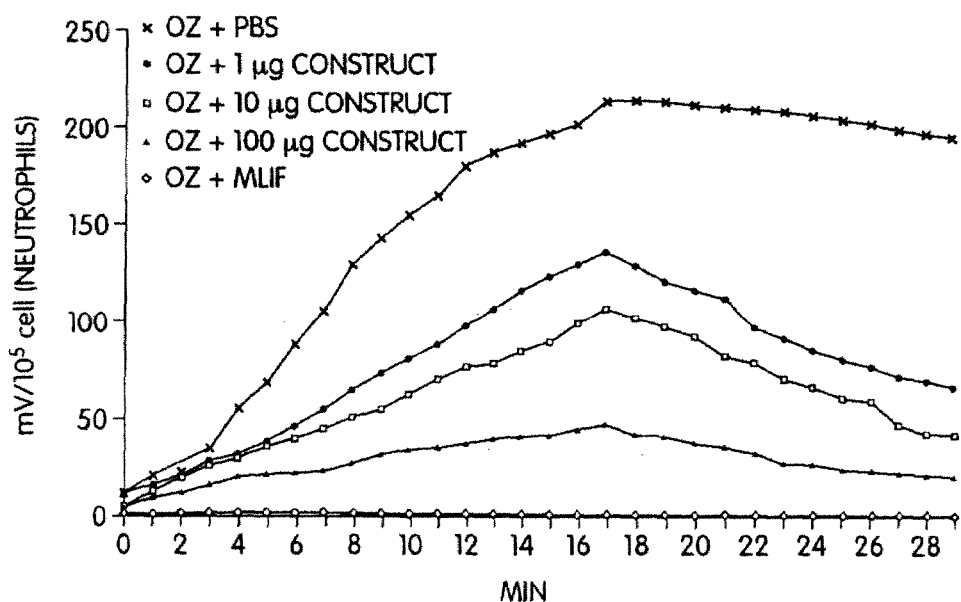
FIG. 3B is a diagram comparing the activity of native MLIF and a synthetic MLIF peptide in inhibiting the respiratory burst of human peripheral blood neutrophils.

In vitro activity of native MLIF and its synthetic custom construct is measured. Inhibition of chemiluminescence in opsonized zymosan activated human peripheral blood MP measured as $mV/10^6$ cells over a 29-30 minute period is shown in FIG. 3A. The same is shown in FIG. 3B using human peripheral blood neutrophils. Six experiments were run in each case, and the averages are shown, deliberately leaving out the s.e.m. in the graphic display, for the sake of clarity. Areas under the curve were significantly ($p<0.01$) different when comparing experimental conditions, except when comparing the curves obtained with the addition of 1 and 10 µg of construct to MP. Inhibition of human peripheral blood MP chemotaxis by native MLIF was comparable to that found when the custom (synthetic) construct was used in similar concentrations. Both values in turn were significantly lower ($p<0.01$) when compared to the normal chemotactic runs (i.e., 100%), or runs using the addition of an axenic medium to the lower compartment of a Boyden chamber as shown in FIG. 3C. The latter experiment was not significantly different when compared to the 100% reference chemotactic run (n=8 for each group).

Example 3

In Vivo Activity of Native MLIF and a Synthetic Construct

Figure 4:
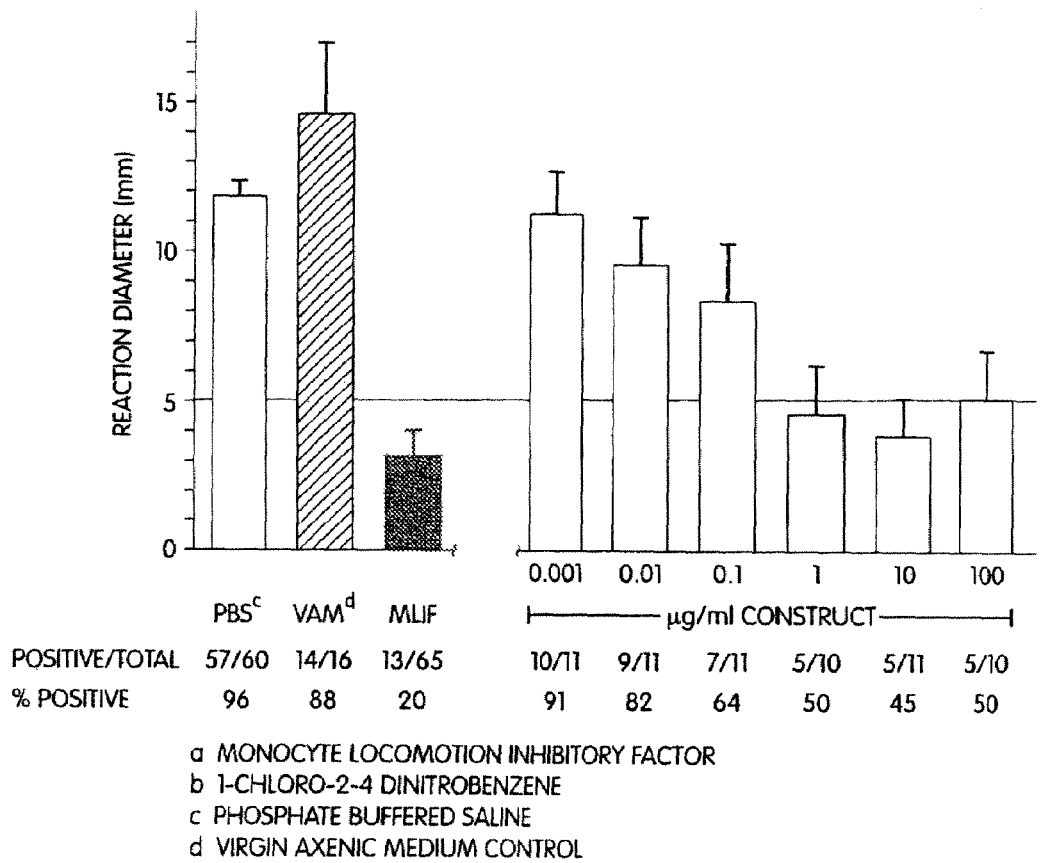
FIG. 4 is a bar diagram showing the effect of native MLIF and a synthetic MLIF peptide for the inhibition of the dinitrochlorobenzene ("DNCB") skin reaction in guinea pigs.

FIG. 4 shows the inhibition of delayed hypersensitivity skin contact dermatitis to DNCB in guinea pigs. The reaction is measured in mm diameter against the eliciting dose, or as positive or negative reactions of the same with a cut-off criterium of 5 mm in diameter. Using either criteria, native MLIF, as well as 1, 10 or 100 µg/ml injections of the custom construct, were significantly different ($p<0.001$) when compared to the effect of the pyrogen-free PBS (phosphate buffered saline, pH 7.4), or virgin axenic medium (VAM) control, but were otherwise comparable among them. The histology of the native MLIF or custom construct inhibited reactions was similar, and clearly revealed a scarce mononuclear perivascular infiltrate when compared to the normal, non-interfered DNCB reactions.

EQUIVALENTS

Those skilled in the art will recognize, or be able to ascertain using no more than routine experimentation, many equivalents to the specific embodiments of the invention described herein. Such equivalents are intended to be encompassed by the following claims.

All references cited herein are incorporated by reference in their entirety.

A Sequence Listing is presented below and is followed by what is claimed.

What is claimed is:

1. A method for inhibiting scar formation comprising administering to a subject a pharmaceutical composition comprising the oligopeptide of SEQ ID NO:1 or SEQ ID NO:2.

2. The method of claim 1 wherein the oligopeptide blocks the activity of fibroblast growth factor signaling adaptor.

3. A method for treating an inflammatory condition comprising administering to a subject a pharmaceutical composition comprising the oligopeptide of SEQ ID NO:1 or SEQ ID NO:2.

4. The method of claim 3 wherein the inflammatory condition is rheumatoid arthritis.

5. The method of claim 3 wherein the inflammatory condition is the result of organ transplantation.

* * * * *

```
SEQUENCE LISTING

<160> NUMBER OF SEQ ID NOS: 2

<210> SEQ ID NO 1
<211> LENGTH: 5
<212> TYPE: PRT
<213> ORGANISM: Entamoeba histolytica
<220> FEATURE:
<221> NAME/KEY: PEPTIDE
<222> LOCATION: (1)..(5)

<400> SEQUENCE: 1

Met Gln Cys Asn Ser
1               5

<210> SEQ ID NO 2
<211> LENGTH: 5
<212> TYPE: PRT
<213> ORGANISM: Entamoeba histolytica
<220> FEATURE:
<221> NAME/KEY: PEPTIDE
<222> LOCATION: (1)..(5)

<400> SEQUENCE: 2

Met Pro Cys Asn Ser
1               5
```